United States Patent
Streeter et al.

(10) Patent No.: US 6,890,330 B2
(45) Date of Patent: May 10, 2005

(54) INTRACARDIOVASCULAR ACCESS (ICVATM) SYSTEM

(75) Inventors: Richard B. Streeter, Winchester, MA (US); John R. Liddicoat, Sewickley, PA (US); Todd F. Davenport, Andover, MA (US)

(73) Assignee: Viacor, Inc., Danvers, MA (US)

( * ) Notice: Subject to any disclaimer, the term of this patent is extended or adjusted under 35 U.S.C. 154(b) by 231 days.

(21) Appl. No.: 10/014,699

(22) Filed: Oct. 26, 2001

(65) Prior Publication Data

US 2002/0138044 A1 Sep. 26, 2002

Related U.S. Application Data

(60) Provisional application No. 60/243,869, filed on Oct. 27, 2000.

(51) Int. Cl.[7] .............................................. A61B 17/00
(52) U.S. Cl. .......................................... 606/1; 604/23
(58) Field of Search ........................... 604/175, 164.01, 604/23, 24, 26, 29, 30, 289, 174; 606/1; 600/21

(56) References Cited

U.S. PATENT DOCUMENTS

| 5,082,005 A | 1/1992 | Kaldany |
| 5,316,541 A | 5/1994 | Fischer |
| 5,336,171 A | 8/1994 | Sugarbaker |
| 5,947,922 A | 9/1999 | MacLeod |
| 6,024,736 A | 2/2000 | de la Torre et al. |

Primary Examiner—LoAn H. Thanh
(74) Attorney, Agent, or Firm—Pandiscio & Pandiscio

(57) ABSTRACT

Apparatus is disclosed for providing access to a functioning vascular system of a patient, the apparatus comprising: a main body having sidewalls defining an interior region and an exterior region, a bottom end and a top end; a base being formed at the bottom end of the main body, securing means being configured on the base so as to allow attachment and formation of a seal between the base and the functioning vascular system of the patient, and the base being configurable to provide a passageway from the interior region of the main body to the functioning vascular system of the patient; and a cover being formed at the top end of the main body, wherein the cover provides a barrier between the interior region and the exterior region at the top end of the main body.

27 Claims, 16 Drawing Sheets

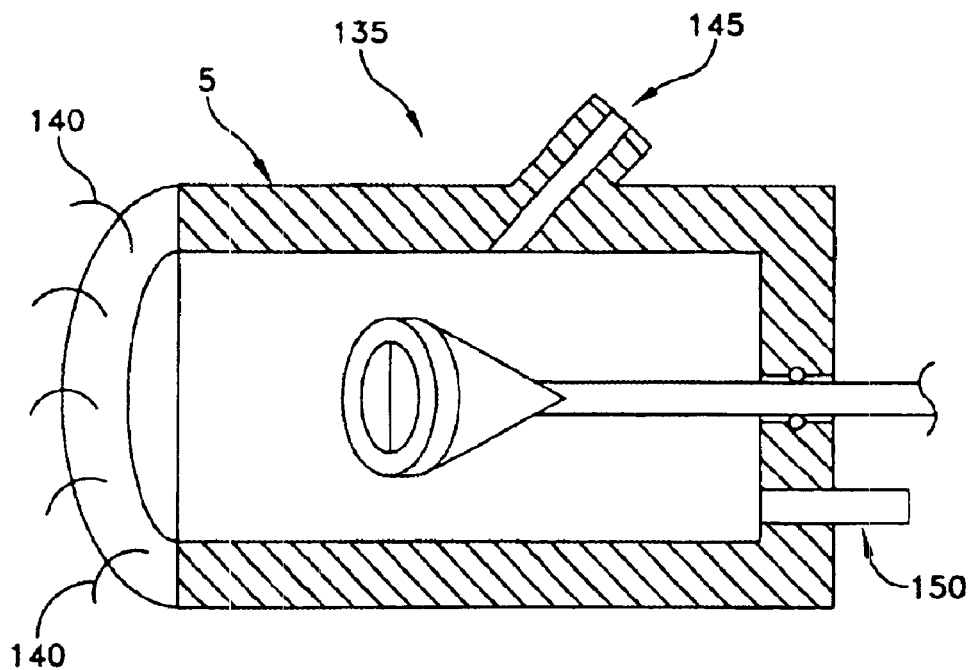
FIG. 16
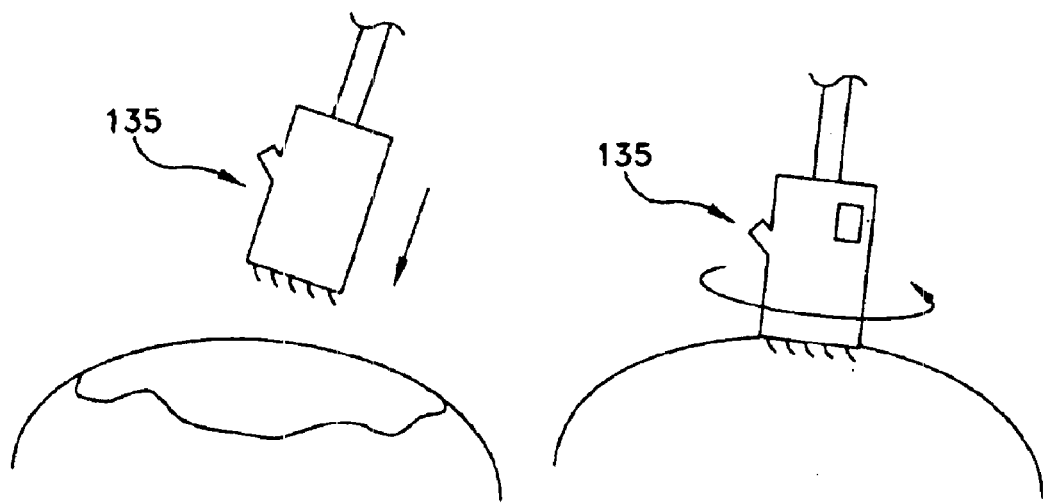
FIG. 17
FIG. 18

INTRACARDIOVASCULAR ACCESS (ICVA™) SYSTEM

REFERENCE TO PENDING PRIOR APPLICATIONS

This patent application claims benefit of prior U.S. Provisional Patent Application Ser. No. 60/243,869, filed Oct. 27, 2000 by Richard B. Streeter et al. for INTRACARDIOVASCULAR ACCESS (ICVA™) SYSTEM, which patent application is hereby incorporated herein by reference.

FIELD OF THE INVENTION

This invention relates to medical devices and procedures in general, and more particularly to medical devices and procedures relating to the cardiovascular system.

BACKGROUND OF THE INVENTION

In standard surgical practice, access to cardiac valves and internal cardiac structures is achieved with the use of cardiopulmonary bypass cardiac arrest and incision into the arrested heart or aorta. Using currently available technology, all cardiac valvular operations require such an approach.

It is well-known that cardiopulmonary bypass and cardiac arrest are associated with significant morbidity and mortality. Recognition of the damaging effects of cardiopulmonary bypass has been the impetus for important advances in beating heart coronary artery bypass grafting. To date, however, it is believed that there are no clinically applicable techniques to perform cardiac valve surgery without using a heart-lung machine. Therefore, cardiac valve surgery currently requires a major operation that includes all of the complications attributable to cardiopulmonary bypass.

In prior U.S. Provisional Patent Applications Ser. Nos. 60/117,599, filed on 27 Jan. 1999, 60/152,135, filed on 25 Aug. 1999, 60/161,934, filed on 28 Oct. 1999, 60/215,542, filed on 30 Jun. 2000, and 60/230,756, filed on 7 Sep. 2000, and in pending PCT Patent Application No. PCT/US00/02126, filed on 27 Jan. 2000, which patent applications are hereby incorporated herein by reference, there are disclosed various devices and procedures to facilitate cardiac valve surgery on a beating heart. An important part of any such system is a safe technique for establishing direct intracardiovascular access to the heart, cardiac valves, and the so-called great vessels. Such access must allow the safe introduction of instruments into the cardiovascular system, prevent entry of air into the cardiovascular system, and prevent excessive bleeding. In this respect it should be appreciated that it is generally essential to avoid the introduction of air into the vascular system of the patient, since this could result in serious complications, or even death, for the patient. Another important part of the invention is to enable the simplified opening and closure of incisions into the cardiovascular system.

SUMMARY OF THE INVENTION

In accordance with the present invention, there is provided a system which is adapted to facilitate safe intravascular access to any cardiac or vascular structure. The system is attached to the cardiovascular structure, using suture or sutureless fixation. Instruments may then be introduced into the system. The system is then partially or completely filled with saline, carbon dioxide, or other substance so as to provide an air-free environment, while also purging air from the previously inserted devices. The cardiovascular structure is then opened with a scalpel or other cutting instrument which, if desired, may be integral to the system. Valves on the system permit controlled passage of instruments into the cardiovascular system without excessive back bleeding. At the completion of the procedure, the system is removed, in whole or in part, and hemostasis is achieved by a means that may include suturing or stapling. Hemostasis may also occur during, or prior to, removal of the system.

The system is not necessarily a stand alone device. The system's features and function can be incorporated into a surgical instrument, for use in vascular surgical procedures.

The system has a specific advantage over cannullae in that large objects or devices may be passed through the system's large opening and into the patient's vascular system. Typically, cannullae only allow access for relatively long, narrow instruments.

By way of further example but not limitation, other specific "beating-heart" applications of the invention can include:

| Access Site | Structure(s) | Purpose |
| --- | --- | --- |
| Right Atrium | Tricuspid Valve | Repair, Replace |
| | Pulmonary Valve | Repair, Replace |
| Left Ventricle | Chordae Tendenae | Repair |
| | Septum | Repair |
| | Aortic Valve | Repair, Replace |
| | Mitral Valve | Repair, Replace |
| | Implanted Pumps | Repair, Clot Removal |
| | Implanted Pacemaker Leads | Removal, Exchange, Functional Testing |
| Right Ventricle | Tricuspid and Pulmonic Valves | Repair, Replace |
| | Septum | Repair |
| | Implanted Pumps | Repair, Clot Removal |
| | Implanted Pacemaker Leads | Removal, Exchange, Functional Testing |

While the system may be used for a wide range of applications, several specific applications are anticipated.

For example, it is anticipated that the system will be affixed to the left atrium of the heart, and/or to the pulmonary veins, in order to allow direct access to the mitral valve. Instruments can then be introduced through the system to perform mitral valve repair or replacement, with or without the use of cardiopulmonary bypass.

Furthermore, in beating heart aortic valve surgery, the system could be affixed to the aorta or to the left atrium. Instruments and an aortic prosthesis could then be introduced to the vascular system of the patient through the system.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 16–18 are views of still another form of the present invention;

DETAILED DESCRIPTION OF THE PREFERRED EMBODIMENTS

Figure 2:
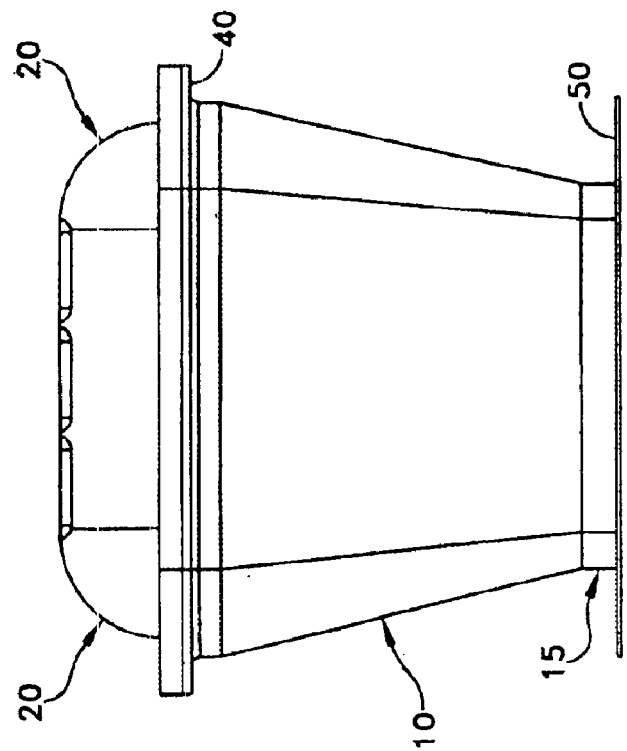
FIG. 2 is a front view of the system shown in FIG. 1.
Figure 1:
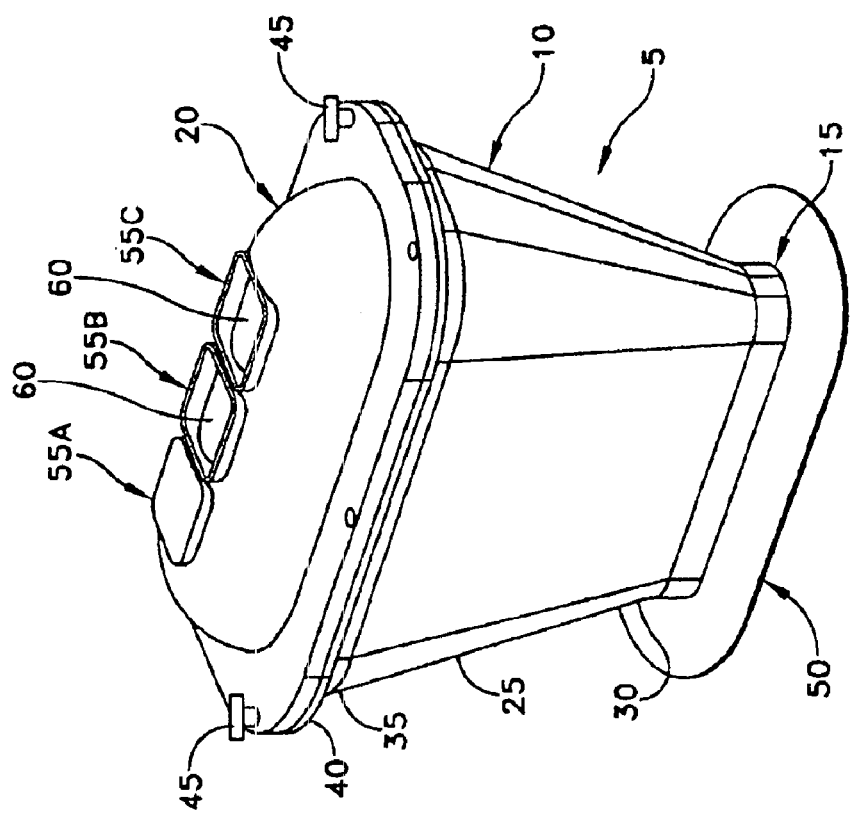
FIG. 1 is a perspective view of a system formed in accordance with the present invention.
Figure 4:
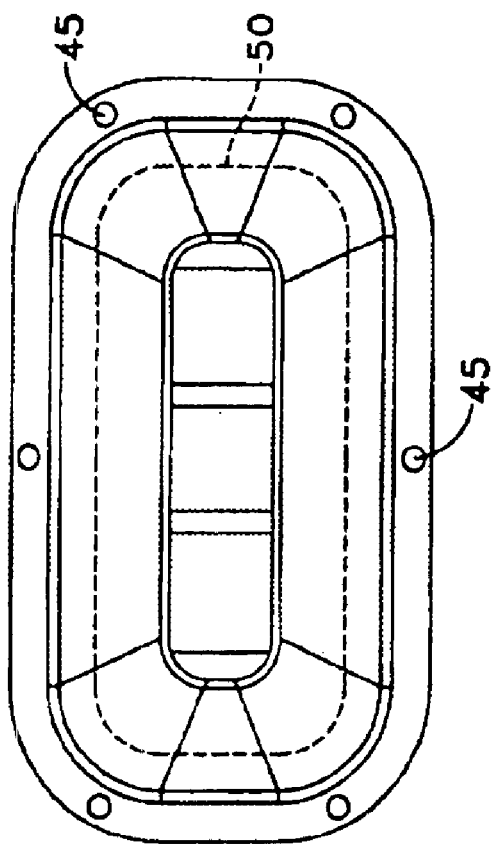
FIG. 4 is a bottom view of the system shown in FIG. 1.
Figure 3:
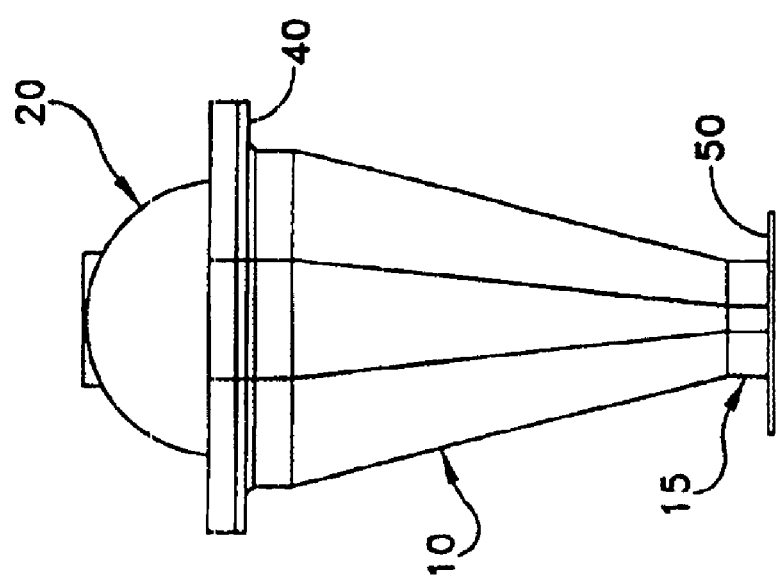
FIG. 3 is a side view of the system shown in FIG. 1.

Looking now at FIGS. 1–4, there is shown a new system 5 which may be used to gain safe and easy air free access to the functioning (or operating) vascular system of a patient. System 5 generally comprises a main body 10, a base 15 and a cover 20.

Main body 10 is a hollow structure and comprises a tapered wall 25 having a bottom end 30 and a top end 35. Tapered wall 25 is preferably formed out of a flexible, clear plastic material, e.g., urethane. The bottom end 30 of tapered wall 25 is connected to base 15 as shown, e.g., by being formed integral with base 15. The top end 35 of tapered wall 25 includes a mount 40 whereby cover 20 may be removably mounted to main body 10, e.g., with thumb screws 45. Mount 40 is preferably formed out a substantially rigid, clear plastic material, e.g., polycarbonate.

Base 15 is a hollow structure which preferably includes a stitching cuff 50 extending around the perimeter of base 15. Stitching cuff 50 permits the system 5 to be secured to a cardiovascular structure, e.g., to the wall of the left atrium of the heart. Base 15 is preferably formed out of a flexible, clear plastic material, e.g., urethane. Stitching cuff 50 is preferably formed out of a clinically acceptable fabric, e.g., Dacron.

Cover 20 is preferably adapted to be removably attached to mount 40 of main body 10. Cover 20 preferably includes several (e.g., three) ports 55 for gaining access to the interior of the system. One of these ports, e.g., port 55A, may comprise the base for a Luer lock fitting or, if desired, may comprise the entire Luer lock fitting. Others of the ports, e.g., ports 55B and 55C, may comprise passageways for instruments. Preferably such instrument ports (e.g., ports 55B and 55C) include penetrable seals 60 of the sort well known in the art for minimizing the flow of fluid through the instrument ports, both when instruments are being passed through the instrument ports and when instruments are not being passed through the instrument ports. Cover 20 is preferably formed out of a substantially rigid, clear plastic material, e.g., polycarbonate.

System 5 may be used to gain safe and easy access to the cardiovascular system of a patient.

By way of example but not limitation, system 5 may be used to gain safe and easy access to the left atrium of a beating heart, whereby to perform a mitral valve replacement or repair while the heart is beating.

In such a procedure, the surgeon first chooses an access site on the surface of the heart, adjacent to the patient's left atrium.

Figure 5A:
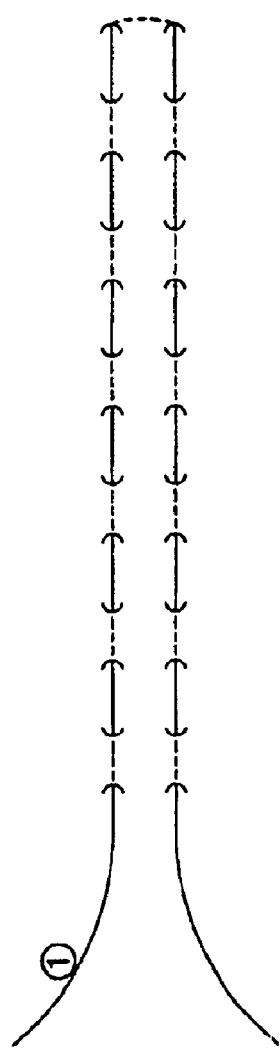
FIGS. 5A–5C illustrate the formation and closure of a pair of pursestring stitches which may be used in conjunction with the present invention.
Figure 5B:
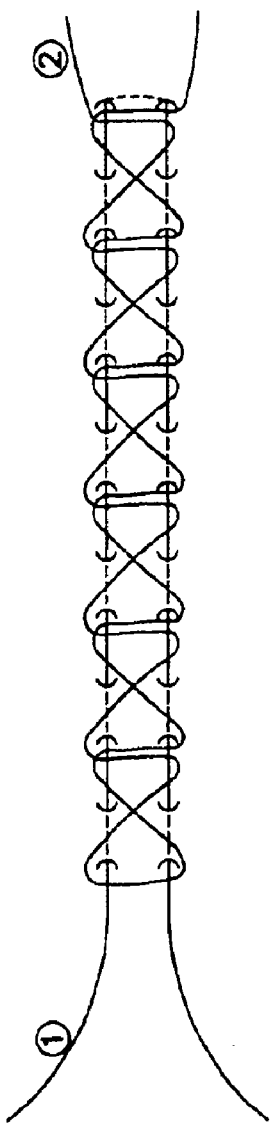
Figure 5C:
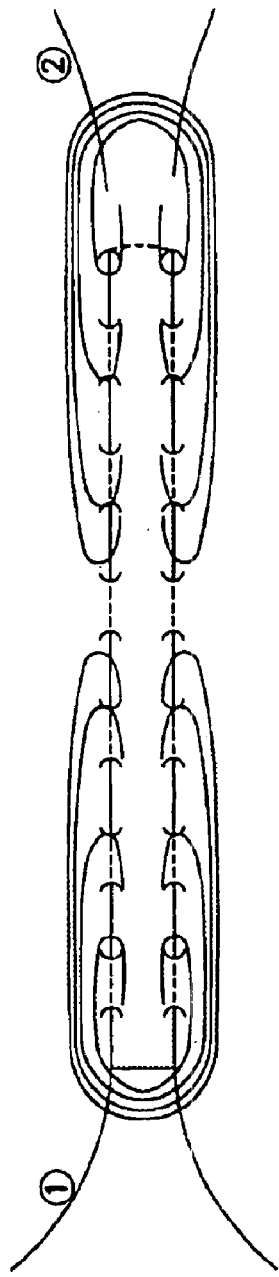

Next, a special running stitch may be pre-placed at the access site. This running stitch is preferably a modified pursestring stitch formed out of two separate pursestring stitches, as shown in FIGS. 5A and 5B which, when subsequently pulled tight, will gather together tissue, as shown in FIG. 5C. The running stitch is placed about the perimeter of the site where the incision will be made, such that, at the conclusion of the procedure, the free ends of the pursestring stitches may be pulled, whereby to close the incision, as will hereinafter be discussed in further detail.

Then the prosthesis (i.e., the artificial valve) is placed in the interior of the system's main body 10, and cover 20 is secured to the top of main body 10 (e.g., with thumb screws 45).

At this point, system 5 is secured to the wall of the heart so that the system's base 15 encircles the running stitch at the incision site. System 5 may be secured to the wall of the left atrium by suturing its stitching cuff 50 to the wall of the beating heart so as to form a substantially fluidtight seal, or a more complex stapling device may be used to secure system 5 to the wall of the left atrium.

Next, carbon dioxide may be introduced into blood lock 5 to displace air from the system. Then a saline source (not shown) is connected to the Luer connector of the system, and the lock is filled with saline.

At this point the system is gently shaken, while attached to the wall of the heart, so as to free up any gas bubbles which may be trapped about the prosthesis. In this respect it will be appreciated that, inasmuch as the interior of system 5 was purged with carbon dioxide prior to being filled with saline, any gas bubbles which might still remain in the interior of the system even after such shaking will be harmless carbon dioxide bubbles, rather than dangerous air bubbles. In a preferred embodiment, a manifold device integral to the system, or temporarily attached thereto, purges air from the system prior to cutting an incision. This manifold device has hoses connected to it from a suction source, a $CO_2$ source and a saline source. The manifold also has an "OFF" position. To purge the blood access system, the surgeon will first apply suction to the system to evacuate most of the air; then fill the system with $CO_2$ to displace any remaining oxygen; and finally fill the system with saline. Any remaining bubbles will mostly be harmless $CO_2$. Alternatively, this device could be a separate manifold tool used to purge any device that might inject air to the circulatory system and be inserted to the blood access system through one of the access seals 60.

A scalpel is then inserted into an instrument port on the system, and an incision is made through the left atrium wall from the inside of the system. This incision is made within the perimeter of the aforementioned running stitch so as to avoid cutting the suture.

Then base 15 of the system, which is flexible and stitched to the wall of the heart, is pulled apart so as to cause the incision to open wide. In this way, a 2 inch incision will yield an approximately 1 inch diameter hole through the wall of the left atrium. However, due to the column of fluid (i.e., saline) contained in system 5, as well as the presence of seals 60, effectively no bleeding will occur.

The prosthetic valve, which was previously placed within the interior of the system, may now be passed through the wall of the left atrium and into position within the heart. Instruments may then be safely and easily passed through the system so as to secure the prosthetic valve in position within the heart.

Once the prosthesis is secured in position within the heart, the instruments are removed from the system, and then the running stitch is pulled tight so as to close the incision in the wall of the left atrium.

Finally, the system is removed from the heart, e.g., by unstitching stitching cuff 50 from the wall of the heart, and then the incision is permanently closed with additional suture or staples while being held closed with the running stitch.

Figure 6:
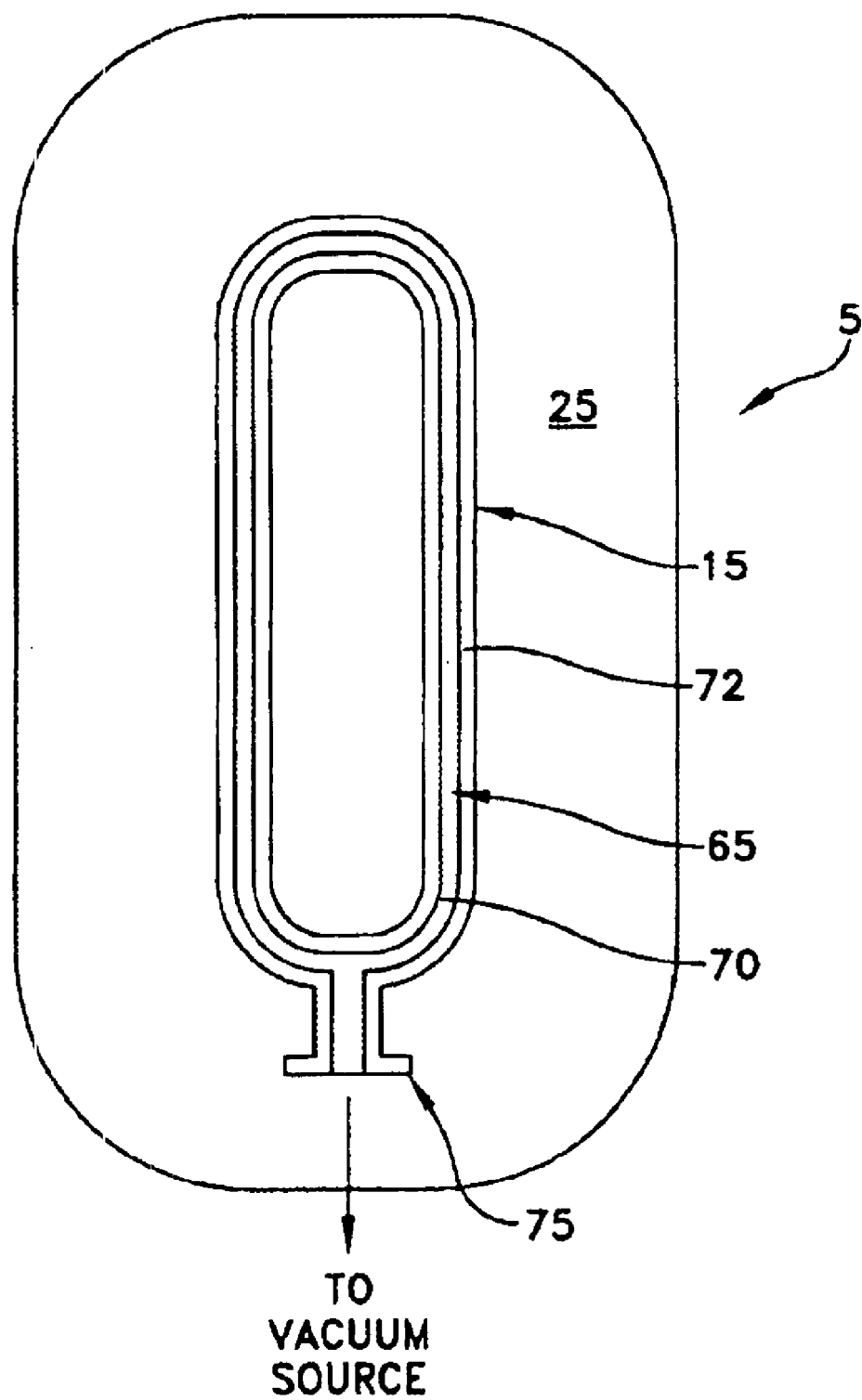
FIG. 6 is a bottom view of an alternative form of the invention.
Figure 7:
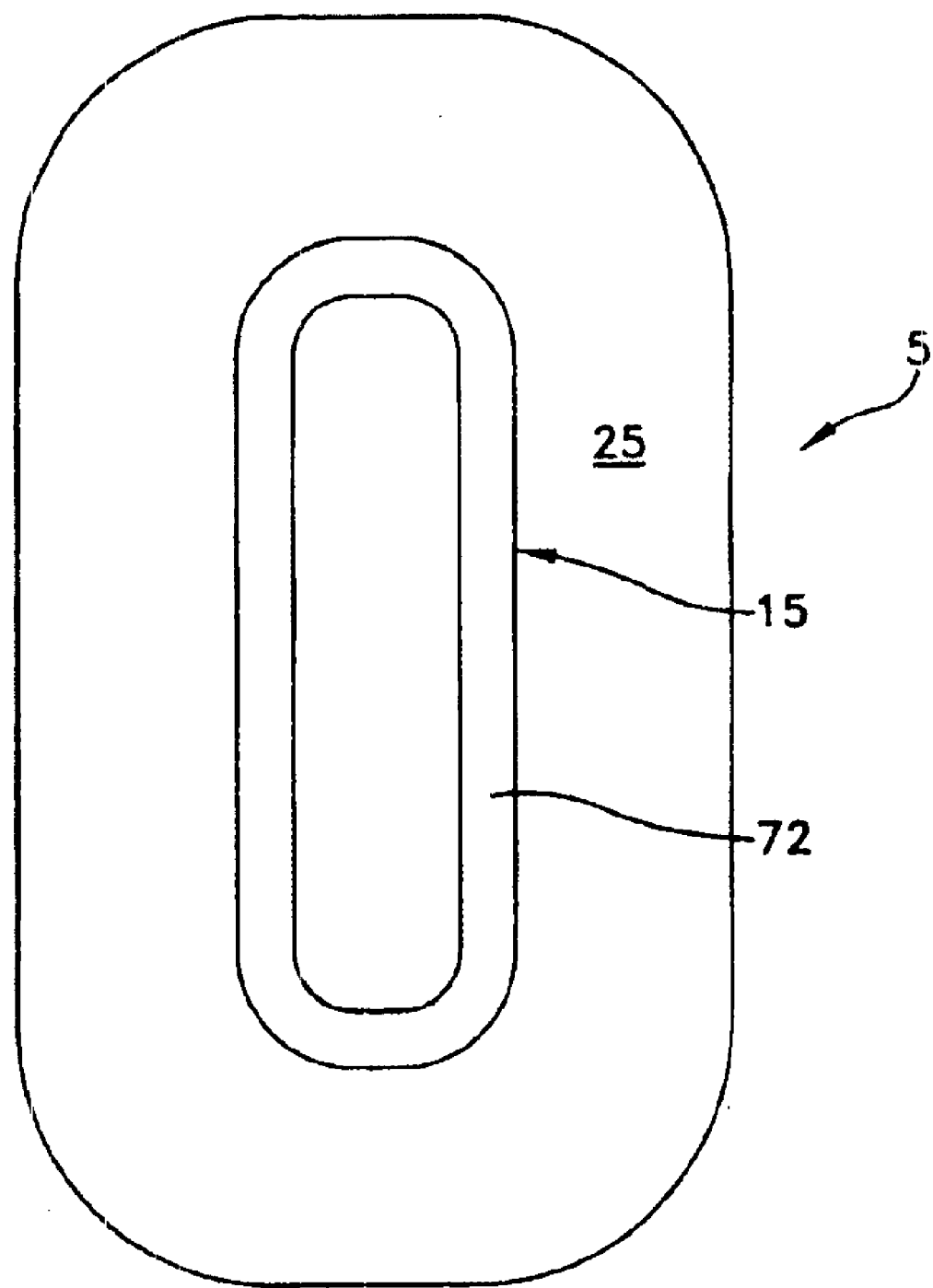
FIG. 7 is a bottom view of another alternative form of the invention.

Looking next at FIGS. 6 and 7, several alternative embodiments are illustrated for attaching system 5 to a cardiovascular structure.

More particularly, in FIG. 6 there is shown a releasable vacuum lock 65 which is adapted to securely attach system 5 to the wall of the heart with a fluidtight seal. Releasable vacuum lock 65 comprises a groove 70 formed in the floor 72 of base 15 and a vacuum fitting 75 communicating therewith, such that when base 15 is positioned against the outer wall of the heart, and a vacuum source is connected to vacuum fitting 75, system 5 may be releasably attached to the wall of the heart through suction.

In another alternative embodiment, and looking now at FIG. 7, the floor 72 of base 15 is adapted to be glued to the outside wall of the heart, whereby to secure the base of system 5 to the wall of the heart. At the conclusion of the cardiac procedure, in order to remove system 5 from the wall of the heart, the system's tapered wall 25 is cut away from base 15. Base 15 may then be left permanently attached to the outside wall of the heart. Any system remnant left attached to the outside of the heart at the conclusion of the procedure should be a soft, flexible material that will not constrain the contractibility of the heart during distole or systole. Additionally, any remnant left on the heart may be over-sewn so as to assure an air-tight seal.

Figure 8:
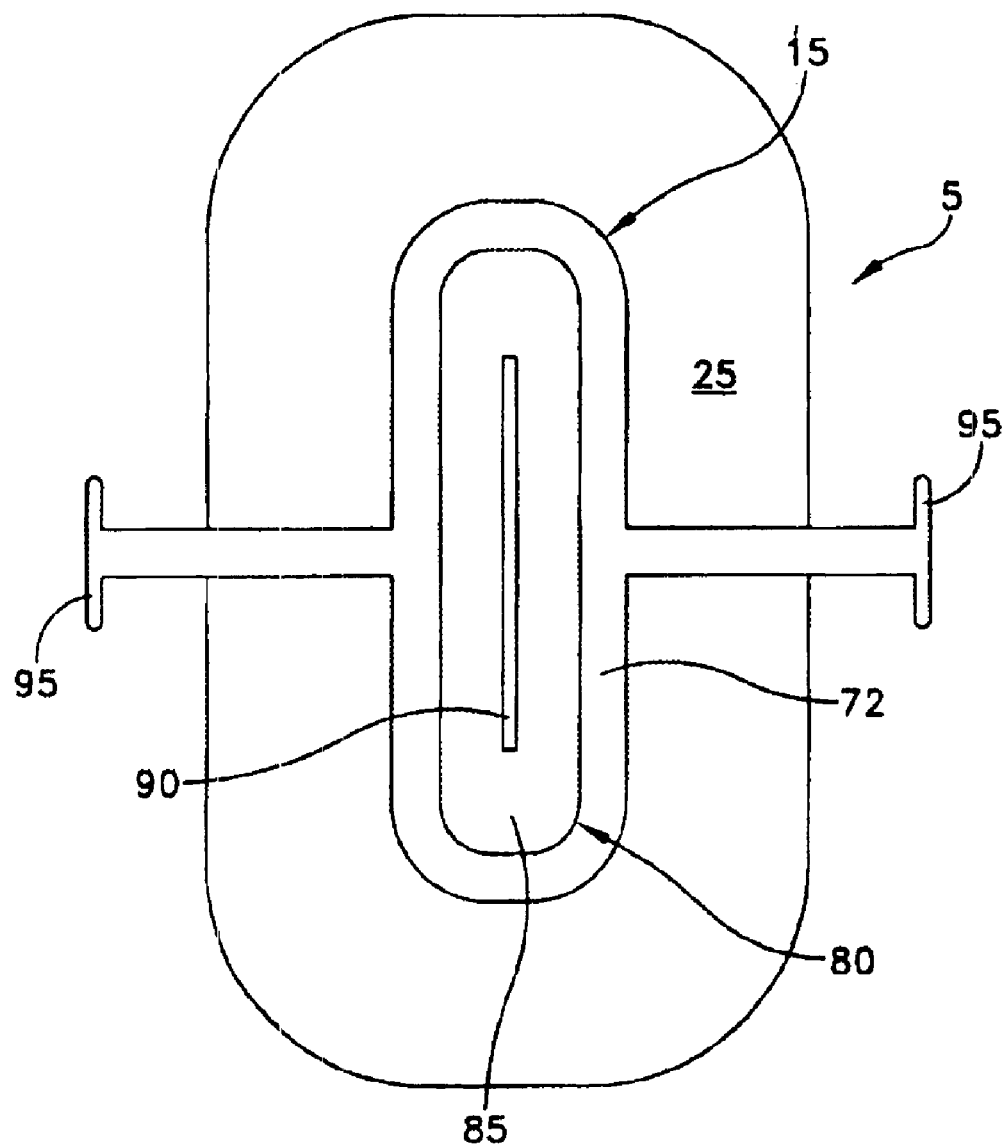
FIG. 8 is a bottom view of still another alternative form of the invention.

Looking next at FIG. 8, a blade guide 80 is provided at base 15 of system 5. Blade guide 80 is adapted to guide a cutting tool (not shown) during an incision through the wall of the heart. To this end, blade guide 80 includes a floor 85 which is resistant to penetration by a cutting blade. This floor 85 may or may not be formed integral with the floor 72 of base 15. Floor 85 includes an opening 90 therein. Opening 90 is initially in the form of a narrow slit so as to act as a guide for a cutting tool when that cutting tool is making an incision through the wall of the heart. This guide may relate to both the perimeter of the incision and the depth of the incision. Floor opening 90 is also adapted to allow larger objects, including prosthetic devices and surgical instruments, to pass through blade guide 80 and then through the wall of the heart. To this end, a pair of tabs 95 are provided for pulling the sides of base 15 outward, whereby to enlarge opening 90 and allow larger objects to pass by the blade guide. In this respect it will be appreciated that inasmuch as the system's base 15 is secured to the wall of the heart when tabs 95 are pulled apart, enlargement of opening 90 will be accompanied by enlargement of the incision as well.

Figure 9:
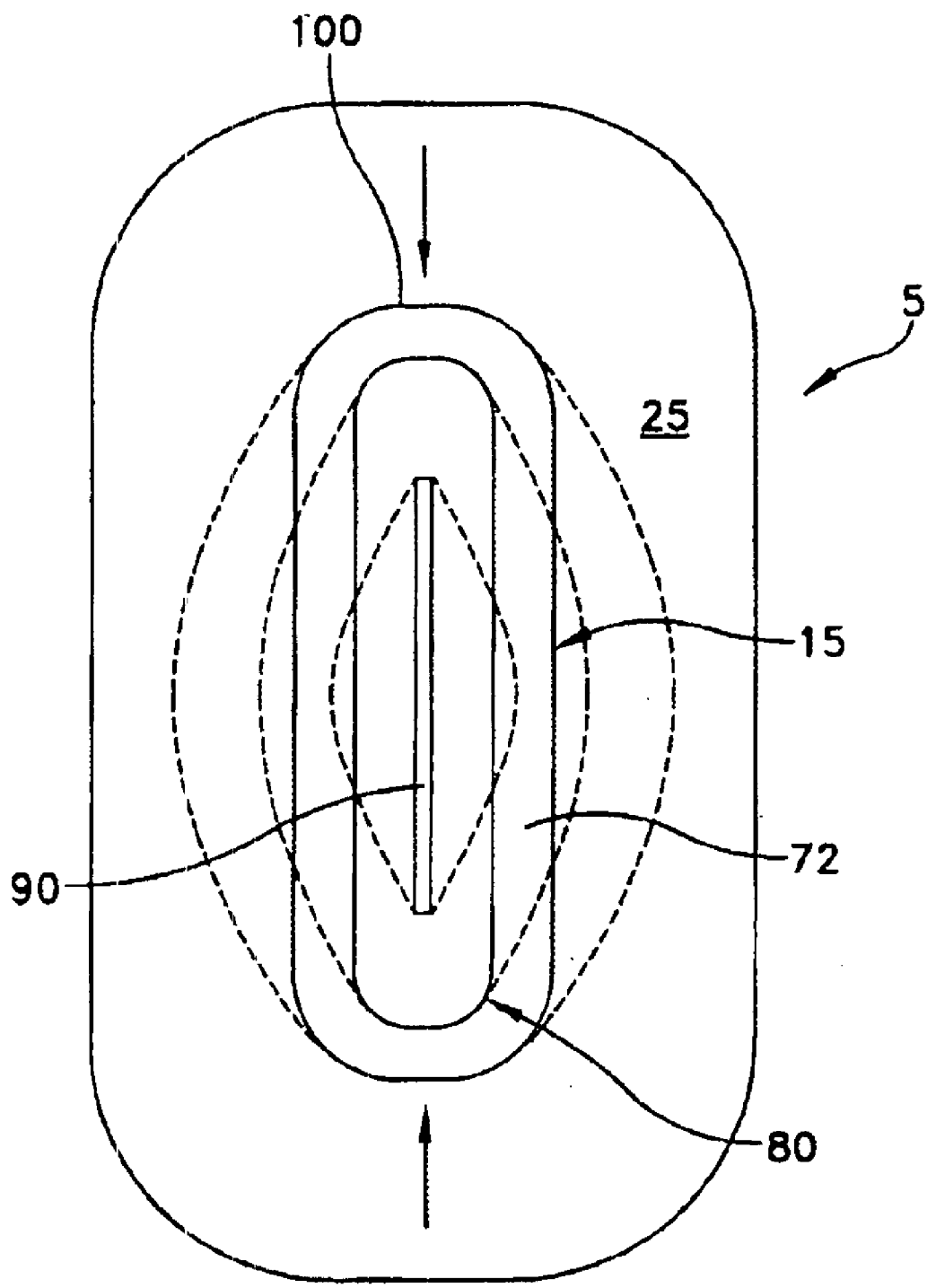
FIG. 9 is a bottom view of yet another alternative form of the invention.

Looking next at FIG. 9, in another alternative embodiment, system 5 has a narrow, flexible base 15 having opposing ends 100, 105 and containing blade guide 80. Base 15 is attached to the wall of the heart as described above using suture cuff 50, releasable vacuum lock 65, or glued floor 72 (this latter configuration is depicted in FIG. 9). An incision is made through blade guide 80 into the wall of the heart. Ends 100, 105 are then pushed toward one another so as to expand base 15 of system 5. Expansion of base 15, which is attached to the wall of the heart, increases the openings of both blade guide opening 90 and the incision. A prosthetic device and other objects may then be introduced through the increased opening in blade guide opening 90 and the increased opening of the incision. Blade guide opening 90 and the incision in the wall of the heart may thereafter be closed by simply relaxing the pressure on opening base ends 100, 105. In the preferred embodiment, instruments may be passed through, and manipulated in, the "closed" position of the incision.

Figure 10:
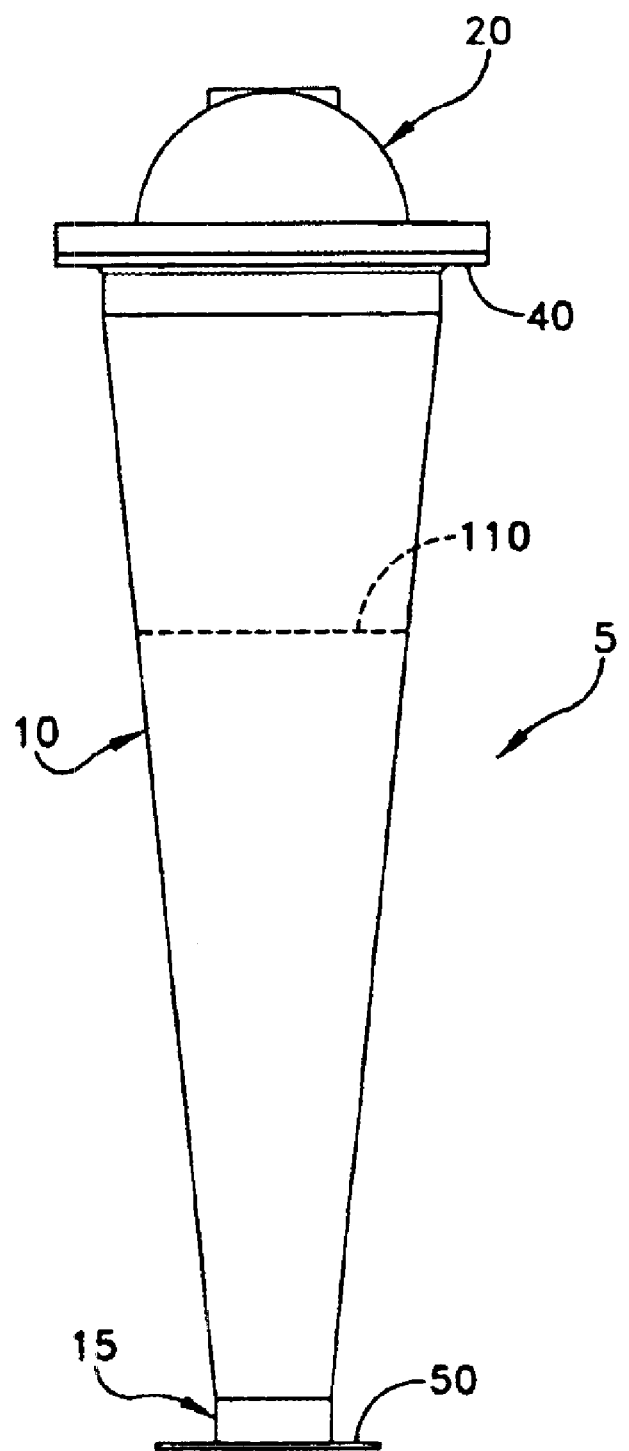
FIG. 10 is a side view of another alternative form of the invention.

In another preferred embodiment, and looking now at FIG. 10, blood lock 5 is provided with a relatively tall main body 10. System 5 is partially filled with fluid and the level 110 of fluid rises and falls with each beat of the heart. This configuration is possible due to the relatively low pressure, i.e., about 5–10 mm Hg, inside the atriums of the heart and the pulmonary veins. This configuration can be advantageous in that a reliable fluid lock is maintained even if cover 20 should be removed intermediate the procedure, e.g., to receive another prosthetic device and/or oversized instruments.

Figure 11:
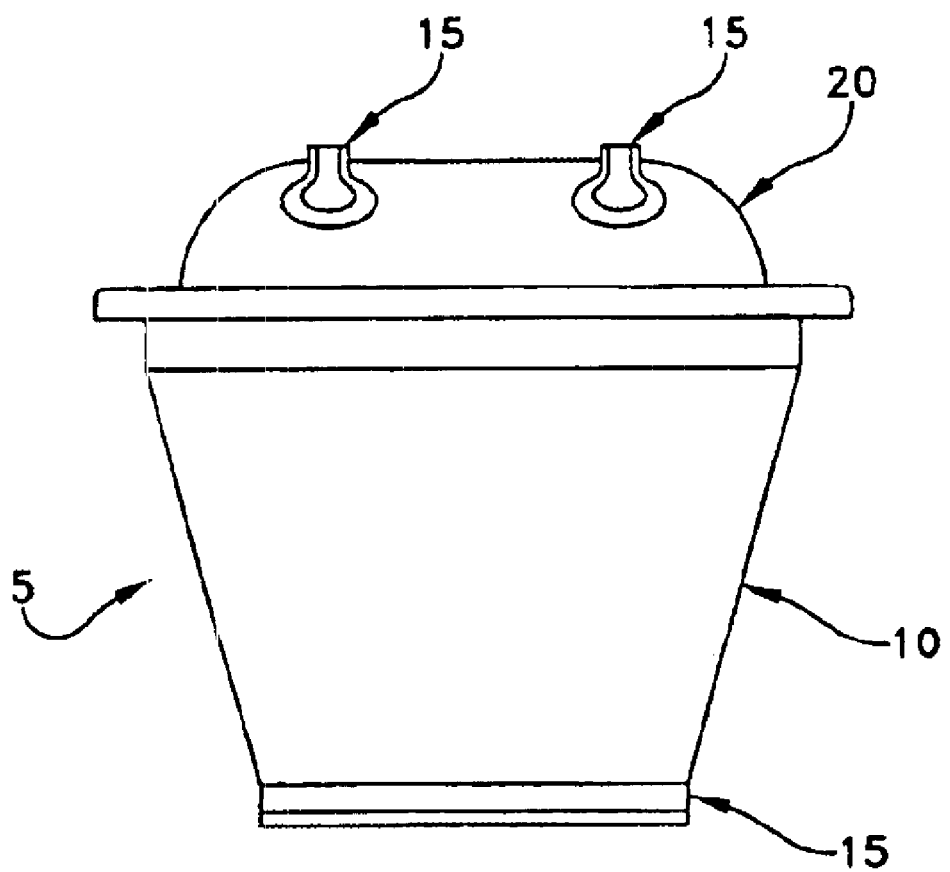
FIG. 11 is a front view of still another alternative form of the invention.

As noted above, blood lock 5 contains seals 60 for selectively closing off its instrument ports 55B and 55C. Examples of such seals are cruciform seals, conical seals and other simple seals. Seals 60 may also include more complex structures such as the articulating seals 115 shown in FIG. 11, whereby to allow greater manipulation of various instruments through the seals.

As also noted above, the incision in the wall of the heart is closed off at the conclusion of the intravascular procedure. In one preferred form of the invention, the running stitch of FIGS. 5A–5C is used. Several additional constructions are described below for closing off the incision in the heart wall.

Figure 12:
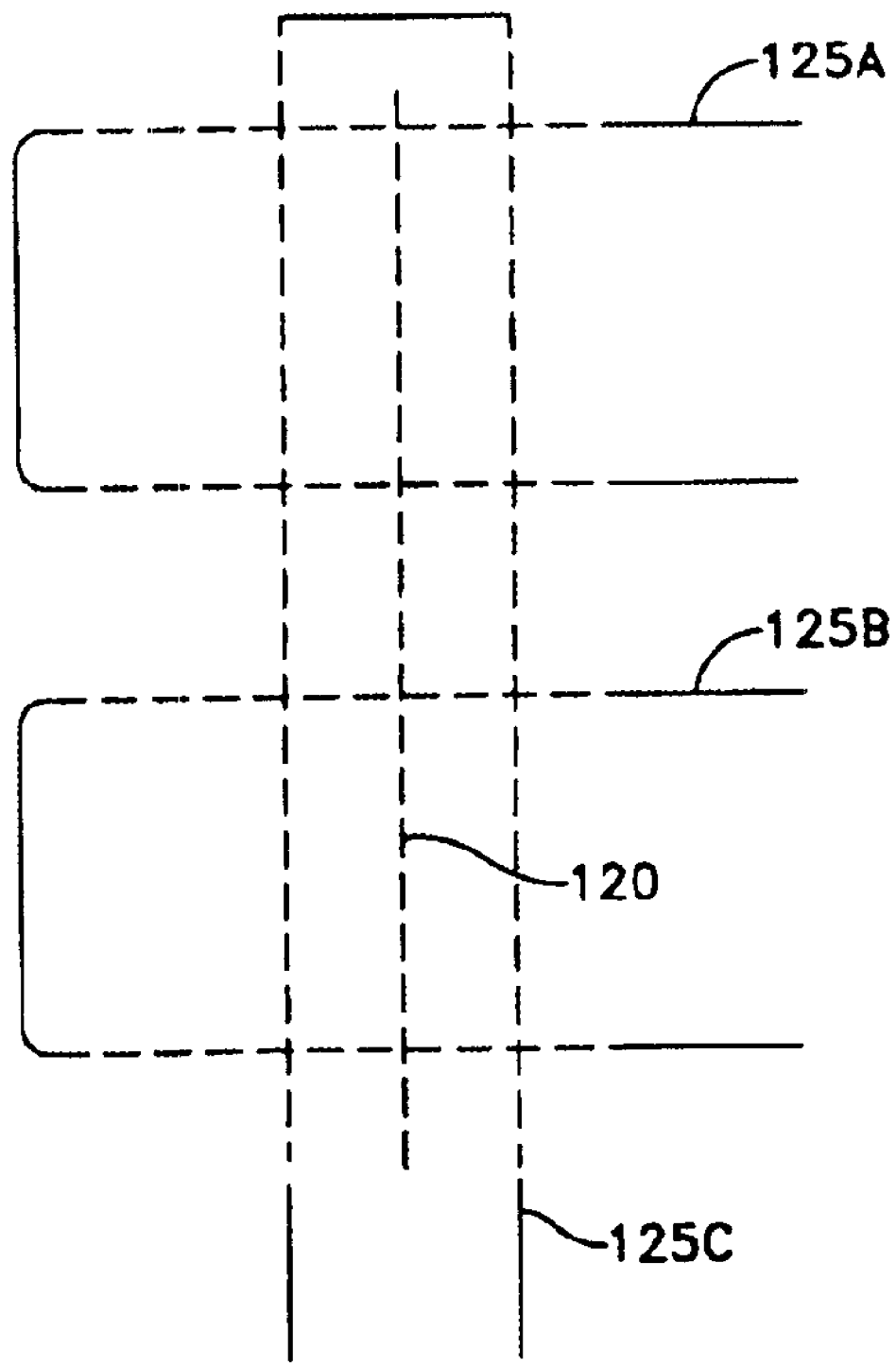
FIGS. 12 and 13 illustrate the formation and closure of alternative pursestring stitches which may be used in conjunction with the present invention.
Figure 13:
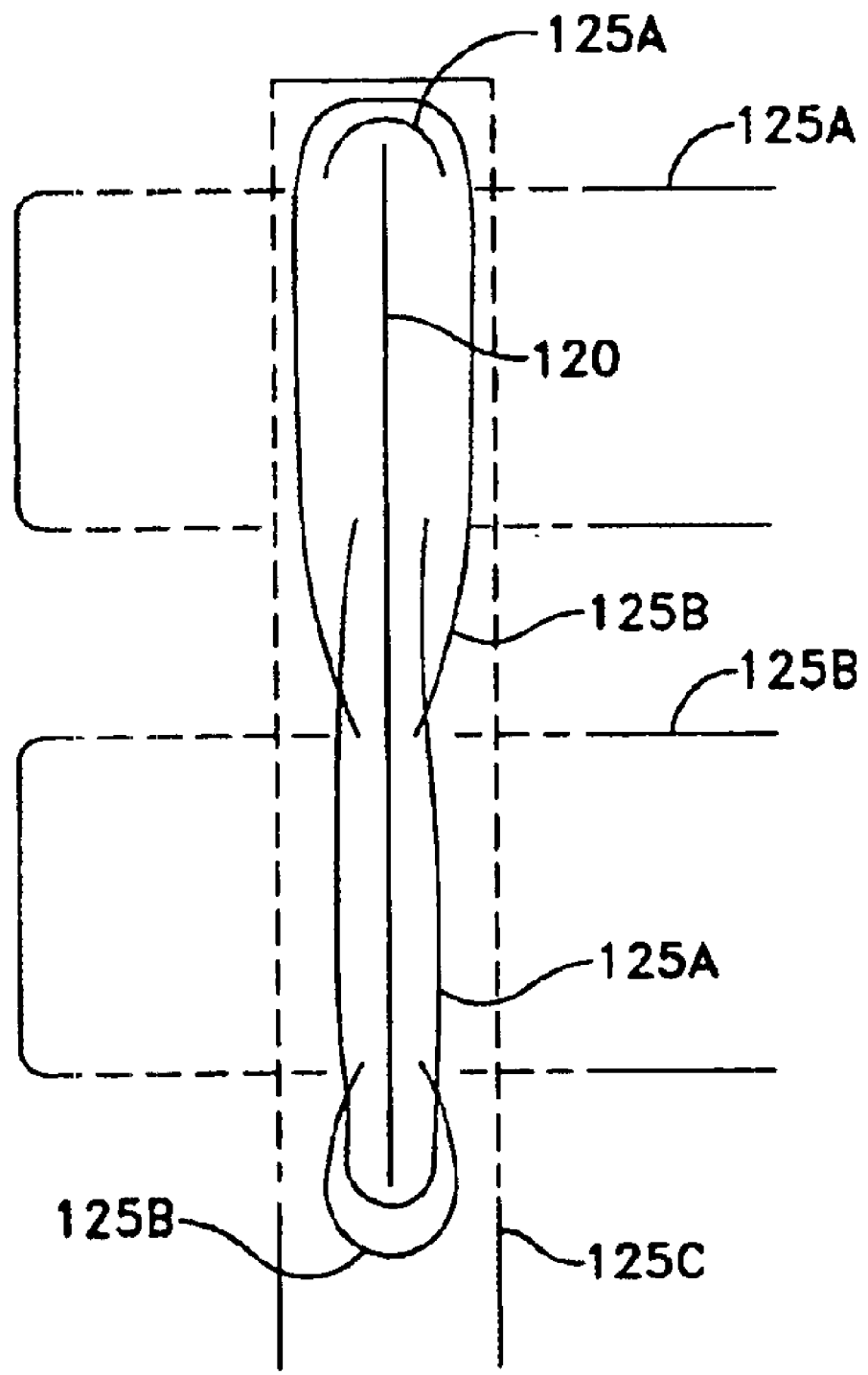

In one preferred construction, and looking now at FIGS. 12 and 13, the incision 120 is preliminarily closed after the intravascular procedure is completed using multiple pursestring stitches 125A, 125B and 125C. Pursestring stitches 125A, 125B and 125C are pre-positioned as shown in FIG. 12. Then the bodies of the pursestring stitches 125A and 125B are pulled so as to open a place for incision 120 (FIG. 13). After attachment of system 5 to the wall of the heart, incision 120 is made within the perimeter of the extended pursestring stitches 125A and 125B, and within the perimeter of pursestring stitch 125C. At the end of the procedure, each pair of pursestring ends are pulled so as to draw each pursestring stitch tight and thereby close incision 120 along its length without causing bunching in the wall of the heart. Then system 5 is removed as described above.

Figure 14:
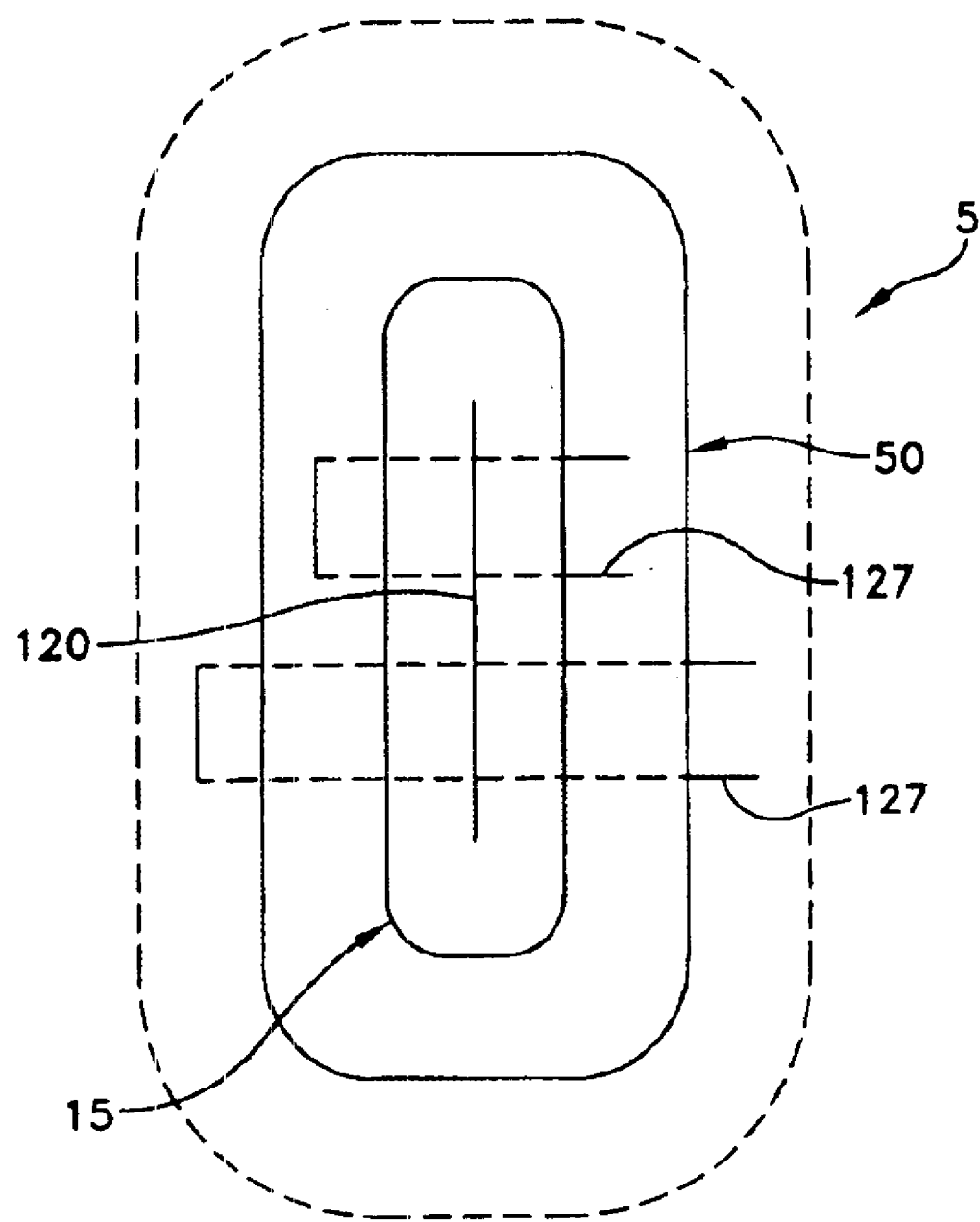
FIG. 14 is a schematic bottom view showing an alternative method for closing an incision at the conclusion of the procedure.

In another preferred embodiment, the incision is closed off by suturing prior to removal of system 5 from the wall of the heart, as illustrated in FIG. 14. In this case, instead of pre-positioning a closing suture, such as a running stitch, in the region where the system will be placed, system 5 is simply attached to the wall of the heart. At the conclusion of the intravascular procedure, incision 120 is sutured closed by simply placing sutures 127 through, or outside of, system 5. After incision 120 is sutured closed, all or part of system 5 is removed from the wall of the heart. Additional suturing to close incision 120 may also be preformed after the removal of system 5.

Figure 15:
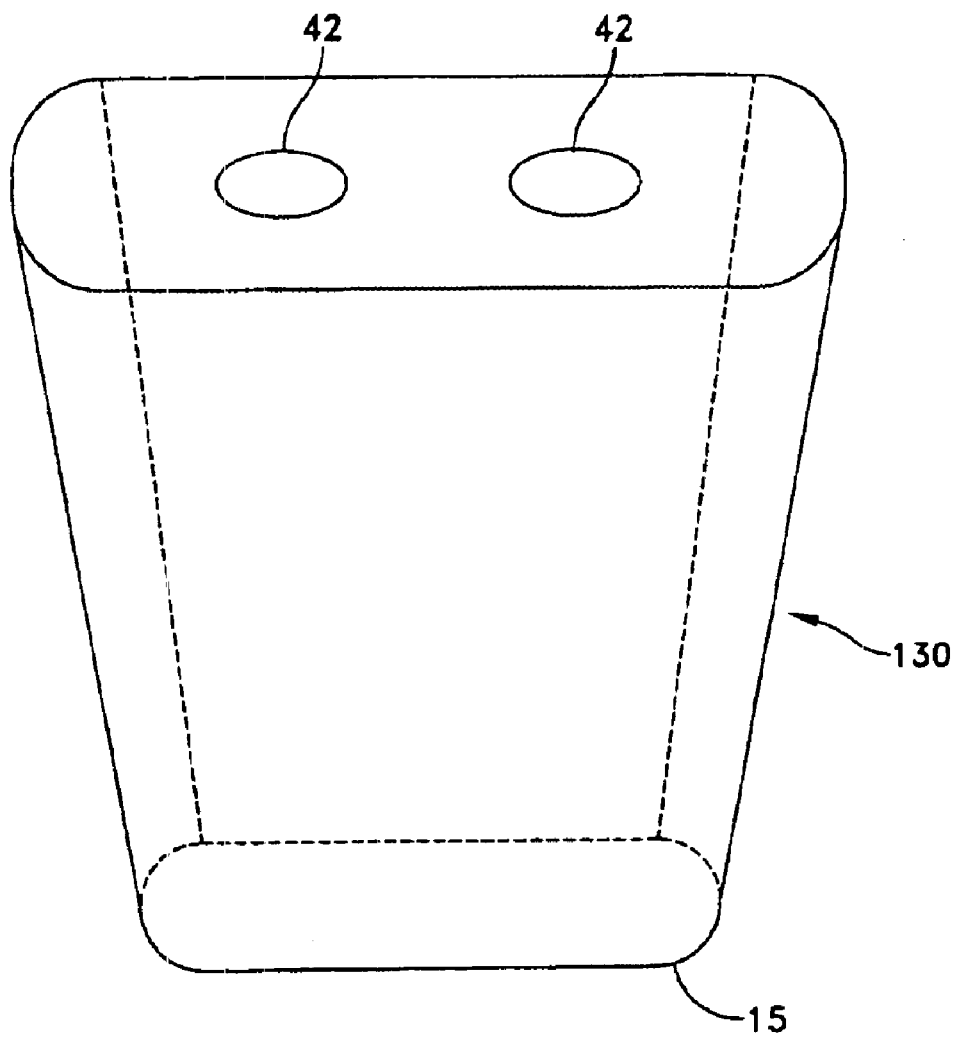
FIG. 15 is a schematic view of yet another form of the present invention.

In another preferred embodiment, cover 20 is formed integral with main body 10 so as to form a closed container 130, shown in FIG. 15. Base 15 is open so as to allow introduction of a prosthesis to the interior of the system prior to the attachment of the system to the wall of the heart. Closed container 130 includes one or more ports 42 to introduce instruments during the intravascular procedure. After attachment of base 15 to the wall of the heart, ports 42 are the only exposure to the outside environment. This configuration may provide a greater integrity of system 5 as cover 20 cannot be removed during the procedure, however, the prosthesis cannot be changed during the intravascular procedure due to the permanent closure of the top end of the system.

In addition to the foregoing, the container 130 shown in FIG. 15 can be formed with a closed bottom wall. In this configuration, the prosthesis is pre-loaded into container 130 at the time of manufacture; thereafter, during use, after the container 130 has been filled with saline, a sharp cutting instrument is introduced through a port 42 and used to simultaneously cut through the system's closed bottom wall and the wall of the heart. Furthermore, if desired, container 130 could be pre-filled with saline at the time of manufacture, and its closed bottom wall could be pre-coated with an adhesive at the time of manufacture, with the adhesive being covered by a peel-off tab until use.

Now looking at FIGS. 16–18, the system 5 may also be formed as part of a tool 135. Tool 135 includes hooks 140 to secure tool 135 to the wall of the heart. An access port 145 is provided for insertion of a scalpel, and a port 150 is provided for connection to a purge line. Tool 135 is used by simultaneously plunging and turning hooks 140 into the wall of the heart so as to secure tool 135 to the heart (FIG. 18).

Figure 19:
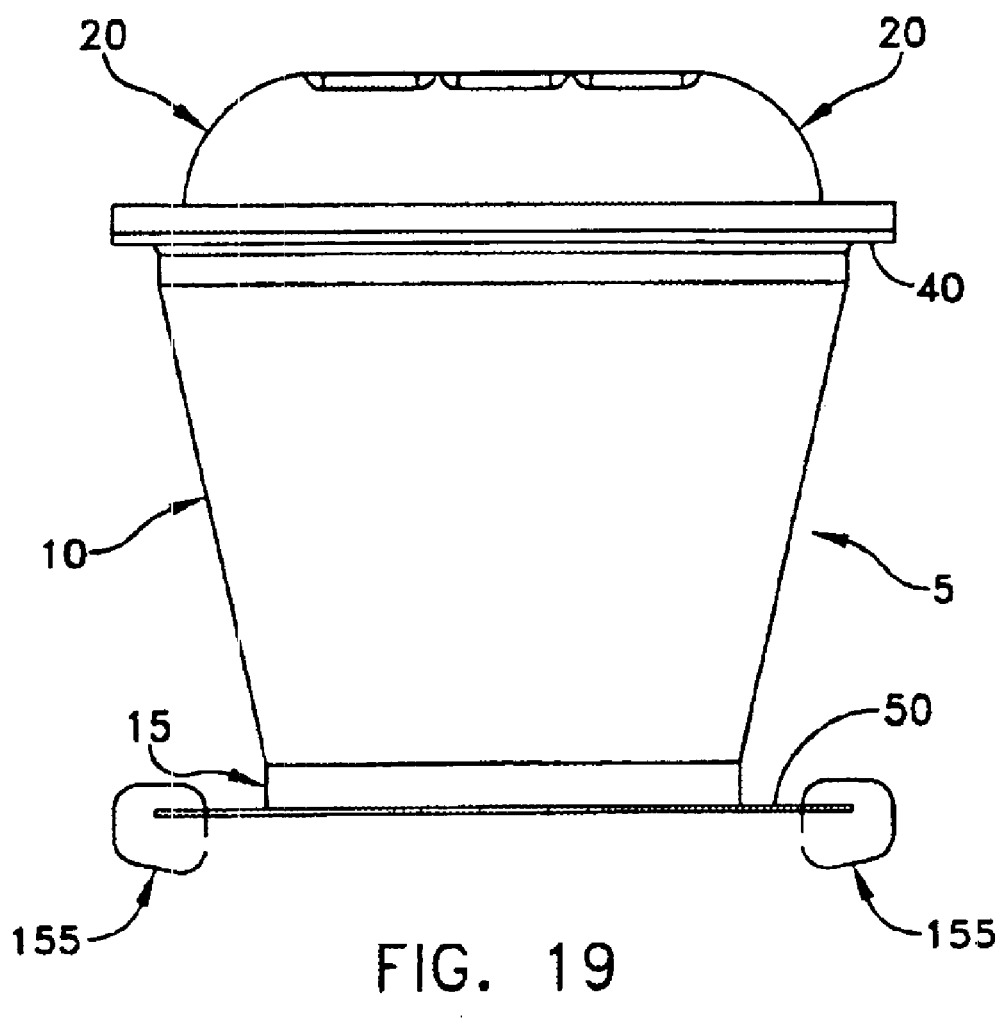
FIG. 19 is a front view of the present invention, showing staples attaching the system to tissue.

Now looking at FIG. 19, a system 5 is shown with staples 155 delivered to its stitching cuff 50 so as to secure the system to the wall of the heart. Staples 155 may be delivered by a complex stapling device.

Figure 20:
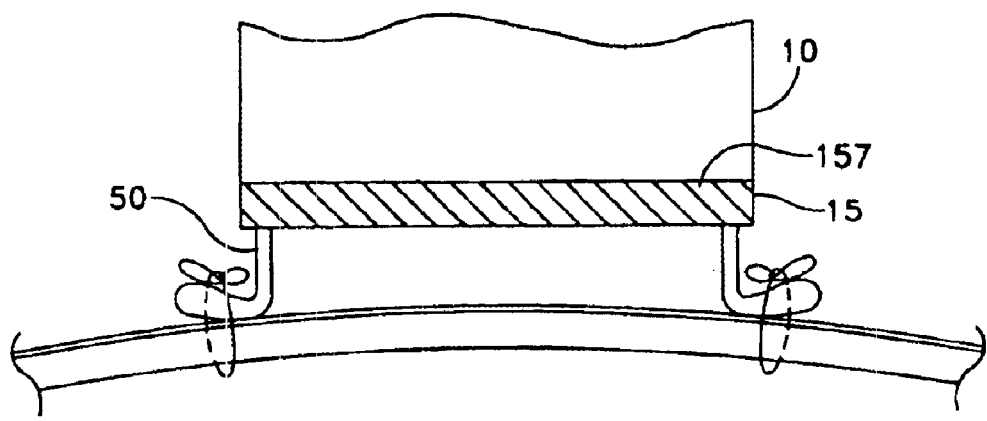
FIGS. 20 and 21 are views of an alternative device and method to close an incision at the conclusion of the procedure.
Figure 21:
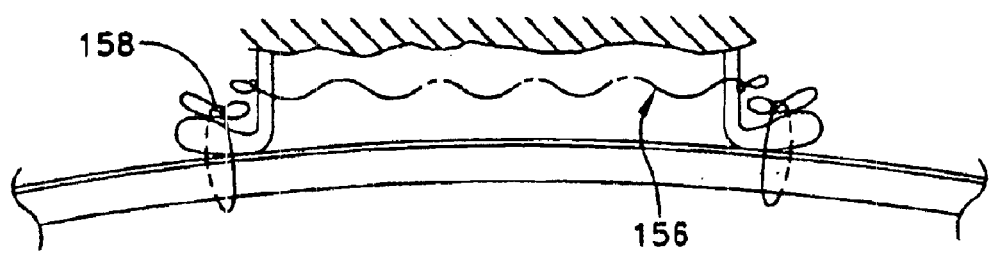

FIGS. 20 and 21 detail an alternative device and method to close the surgical incision 120. Without limiting the scope of this invention, the preferred embodiment of this device and method is to directly close stitching cuff 50 with suture 156, below the base 15 and as close to the surgical incision 120 as possible, which in turn holds incision 120 closed during the healing process. The closed stitching cuff 50 may then either be cut away or detached from the base 15 above cuff closing suture 156 but below the stitching cuff interface 157. This interface 157 is created during the manufacturing process and may be any one of a number of fixation methods such as sewing, stapling, insert molding or mechanical crimping. This interface may also be the position where the implanted stitching cuff 50 is removed from the base 15. FIG. 21 shows the implanted stitching cuff 50, closed with closing Suture 156. It is also envisioned that closing suture 156 may be one of many closing mechanisms such as wire, staples or adhesives. Additionally, in case of an emergency, the surgeon may quickly close the open incision 120 by placing a large hemostat across the stitching cuff along the same path of closing suture 156, as shown in FIG. 21. Additionally, as described earlier, suture cuff 50 may be attached to the surgical site via sutures 158 or hooks 140 or staples 155 or adhesive or other appropriate attaching means.

What is claimed is:

1. Apparatus for providing access to a functioning vascular system of a patient, said apparatus comprising;
   a main body having sidewalls defining an interior region, an exterior region, a bottom end, and a top end;
   a base formed at the bottom end of said main body and having securing means thereon configured for attachment to the vascular system of the patient and configured for formation of a seal between said base and the functioning vascular system of the patient, said base containing an opening therein, the opening configured to provide a passageway from the interior region of said main body to the functioning vascular system of the patient, and said opening of said base being selectively adjustable in attachment to the vascular system of the patient between a first configuration and a second configuration, said first configuration providing said opening with a first given cross-sectional area, said second configuration providing said opening with a second given cross-sectional area, and the second given cross-sectional area being larger than said first given cross-sectional area; and
   a cover attached to the top end of said main body, and configured to provide a barrier between the interior region and the exterior region at the top end of said main body.

2. Apparatus according to claim 1 wherein said sidewalls of said main body are tapered inwardly from said top end to said bottom end.

3. Apparatus according to claim 1 wherein the interior region comprises saline so as to provide an air-free environment therein.

4. Apparatus according to claim 1 wherein the interior region comprises carbon dioxide so as to provide an air-free environment therein.

5. Apparatus according to claim 1 wherein the interior region comprises a solution of saline and carbon dioxide so as to provide an air-free environment therein.

6. Apparatus according to claim 1 wherein said main body comprises a flexible material.

7. Apparatus according to claim 6 wherein said flexible material comprises urethane.

8. Apparatus according to claim 1 wherein said cover is integral with said main body.

9. Apparatus according to claim 1 wherein the top end of said main body comprises a mount, and said cover is removably attachable to said mount on said main body.

10. Apparatus according to claim 9 wherein said mount is formed of a substantially rigid material.

11. Apparatus according to claim 10 wherein the material comprises polycarbonate.

12. Apparatus according to claim 1 wherein the passageway in said base comprises an opening formed therein prior to attachment to the functioning vascular system of the patient.

13. Apparatus according to claim 1 wherein the passageway in said base comprises an opening formed therein after said base is attached to the functioning vascular system of the patient.

14. Apparatus according to claim 1 wherein the securing means comprises a stitching cuff extending around a perimeter of said base.

15. Apparatus according to claim 1 wherein said cover comprises a port therein, said port being configured to permit access between said exterior region and said interior region of said main body.

16. Apparatus according to claim 1 wherein the port comprises a base for a Luer lock fitting.

17. Apparatus according to claim 1 wherein the port comprises an entire Luer lock fitting.

18. Apparatus according to claim 1 wherein the port comprises an instrument passageway.

19. Apparatus according to claim 18 wherein said instrument passageway comprises a penetrable seal.

20. Apparatus according to claim 1 wherein said cover comprises a substantially rigid material.

21. Apparatus according to claim 20 wherein said substantially rigid material comprises polycarbonate.

22. Apparatus according to claim 1 wherein the seal comprises a vacuum seal.

23. Apparatus according to claim 1 wherein the securing means comprises hooks.

24. Apparatus according to claim 1 wherein the securing means comprises an adhesive material.

25. Apparatus according to claim 1 wherein said base comprises a blade guide for forming the passageway from the interior region of said main body to the functioning vascular system.

26. Apparatus according to claim 1 wherein said base is selectively configurable between a first configuration and a second configuration, and wherein the passageway from the interior region of said main body to the functioning vascular system of the patient is substantially closed in the first configuration and the passageway from the interior region of said main body to the functioning vascular system of the patient is substantially open in the second configuration.

27. Apparatus according to claim 26 wherein said main body is selectively configured between the first configuration and the second configuration by squeezing opposed ends of said main body toward one another.

* * * * *